(12) United States Patent
Lundgaard et al.

(10) Patent No.: US 7,918,828 B2
(45) Date of Patent: Apr. 5, 2011

(54) MEDICAL SECURING DEVICE

(75) Inventors: Sabine Lundgaard, Århus V. (DK);
Mads Hemdorff Petersen, Århus C (DK); Kristian Rye Veedfald, Århus C (DK)

(73) Assignee: Health Equipment Denmark APS (DK)

( * ) Notice: Subject to any disclaimer, the term of this patent is extended or adjusted under 35 U.S.C. 154(b) by 554 days.

(21) Appl. No.: 10/580,784

(22) PCT Filed: Nov. 29, 2004

(86) PCT No.: PCT/DK2004/000828
§ 371 (c)(1),
(2), (4) Date: May 25, 2006

(87) PCT Pub. No.: WO2005/051472
PCT Pub. Date: Jun. 9, 2005

(65) Prior Publication Data
US 2007/0142785 A1    Jun. 21, 2007

(30) Foreign Application Priority Data

Nov. 28, 2003 (DK) .............................. 2003 01757

(51) Int. Cl.
*A61M 5/32* (2006.01)
(52) U.S. Cl. ........ 604/174; 604/175; 604/176; 604/177; 604/178; 604/179; 604/180; 248/229.1; 248/73
(58) Field of Classification Search .......... 604/174–180; 248/229.1
See application file for complete search history.

(56) References Cited

U.S. PATENT DOCUMENTS

| 556,209 | A | * | 3/1896 | Quinn ............................. 24/3.11 |
| 1,032,436 | A | * | 7/1912 | Smith .......................... 24/11 CT |
| 2,506,783 | A | * | 5/1950 | Fauteux, Jr. ..................... 24/532 |
| 3,747,166 | A | * | 7/1973 | Eross ............................... 248/75 |
| 4,277,864 | A | * | 7/1981 | Orson, Sr. ........................ 24/327 |
| 4,639,980 | A | * | 2/1987 | Peterson ......................... 24/306 |
| 4,660,555 | A | | 4/1987 | Payton |
| 4,707,906 | A | * | 11/1987 | Posey .............................. 29/453 |
| 4,711,636 | A | * | 12/1987 | Bierman ......................... 604/180 |
| 4,747,626 | A | * | 5/1988 | Hama et al. ..................... 285/308 |
| 4,820,274 | A | * | 4/1989 | Choksi et al. .................. 604/174 |
| 4,835,824 | A | * | 6/1989 | Durham et al. .................. 24/339 |
| 4,907,582 | A | * | 3/1990 | Meyerrose ............... 128/201.11 |
| 4,944,924 | A | * | 7/1990 | Mawhirt et al. ............... 422/104 |

(Continued)

FOREIGN PATENT DOCUMENTS

FR          2 598 625        11/1987

OTHER PUBLICATIONS

International Search Report; PCT/DK2004/000828; Aug. 4, 2005.

*Primary Examiner* — Nicholas D Lucchesi
*Assistant Examiner* — Scott Medway
(74) *Attorney, Agent, or Firm* — Cantor Colburn LLP

(57) ABSTRACT

Device for securing a line such as a medical tube, a catheter, diagnostic wires etc., the device including
  a line retaining part and a base part,
  the line retaining part having at least one groove for accommodating a line, the groove being designed with flexible retaining means,
  the base part including fixing means,
  where the line retaining part and the base part are provided with complementary locking means.

32 Claims, 11 Drawing Sheets

U.S. PATENT DOCUMENTS

| | | | |
|---|---|---|---|
| D314,015 S * | 1/1991 | Hickman, Sr. | D20/27 |
| 4,986,815 A * | 1/1991 | Schneider | 604/180 |
| 4,997,421 A * | 3/1991 | Palsrok et al. | 604/174 |
| 5,188,609 A | 2/1993 | Bayless et al. | |
| 5,267,967 A * | 12/1993 | Schneider | 604/174 |
| 5,318,192 A * | 6/1994 | Rebeyrolle et al. | 215/252 |
| 5,400,776 A | 3/1995 | Bartholomew | |
| 5,413,562 A * | 5/1995 | Swauger | 604/179 |
| 5,470,321 A * | 11/1995 | Forster et al. | 604/174 |
| 5,640,742 A * | 6/1997 | White et al. | 24/3.12 |
| 5,651,522 A * | 7/1997 | Davis et al. | 248/221.11 |
| 5,666,702 A * | 9/1997 | Ming-Chieh | 24/510 |
| 5,795,335 A | 8/1998 | Zinreich | |
| 5,947,931 A | 9/1999 | Biermann | |
| 6,074,368 A | 6/2000 | Wright | |
| 6,134,754 A | 10/2000 | Hansson et al. | |
| 6,247,211 B1 | 6/2001 | Bell | |
| 6,428,514 B1 * | 8/2002 | Goebel et al. | 604/174 |
| 6,438,802 B1 * | 8/2002 | Beeman et al. | 24/135 R |
| 6,523,231 B1 * | 2/2003 | Lassiter | 24/339 |
| 6,641,093 B2 * | 11/2003 | Coudrais | 248/73 |
| 6,804,866 B2 * | 10/2004 | Lemke et al. | 24/338 |
| 6,925,689 B2 * | 8/2005 | Folkmar | 24/499 |
| 7,134,433 B2 * | 11/2006 | Sato | 128/201.11 |
| 2003/0026787 A1 * | 2/2003 | Fearnot et al. | 424/93.7 |
| 2003/0057277 A1 * | 3/2003 | Kimura et al. | 235/449 |
| 2004/0145892 A1 * | 7/2004 | Kellough | 362/208 |
| 2008/0132848 A1 * | 6/2008 | Wright et al. | 604/174 |

* cited by examiner

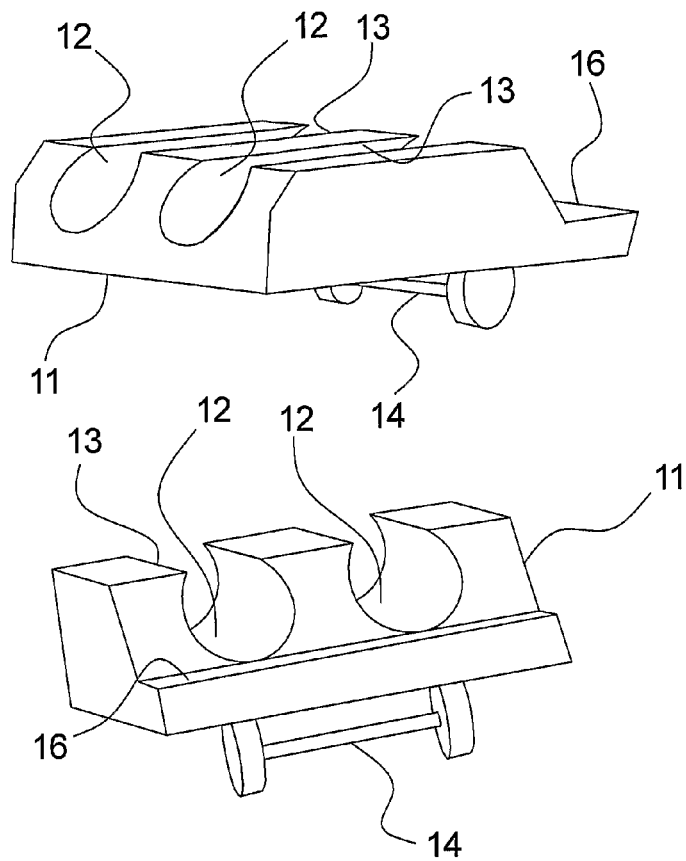
*Fig. 1a*
*Fig. 1b*
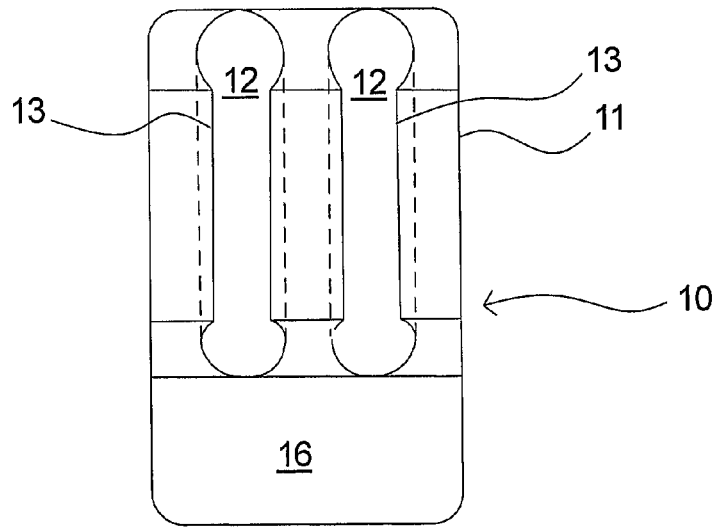
*Fig. 2a*

MEDICAL SECURING DEVICE

FIELD OF THE INVENTION

The invention relates to a device for securing a line such as a tube, a wire etc. and in particular a medical line such as a catheter, electric wires for e.g. diagnostic monitoring equipment etc.

Further, the invention relates to uses of such a device.

DESCRIPTION OF RELATED ART

In the medical field it is common practice when the treatment, diagnosis etc. of a patient involves use of catheters to use medical or surgical tape, for example Micropore™ surgical tape, in order to maintain the catheter in place on the skin and/or the clothes of the patient. However, this practice suffers from a number of drawbacks, one of which being a less than secure fixation of the catheter to the patient. For example, the tube(s) may fall off or shift during use, which may result in dangerous situations, for example during dialysis, where hemolysis may be caused. Further, the surgical tape can be difficult to handle by nurses and other medical staff persons, in particular since such persons often use gloves, e.g. rubber gloves, in such situations. Still further, the comfort to both the patient and the e.g. nurse is less than optimal when using medical tape for the securing of catheters and other medical lines, tubes etc. Also, the use of such tape may be a hygienic liability since the tape may collect dust, dirt and other particles on the adhesive surface. Further, some persons may be allergic to such tapes and/or adhesives, and there may be a risk that allergic distresses will develop with long term use.

Other solutions that relate to the problem of securing medical tubes are disclosed in the prior art.

Thus, FR 2 598 625 A1 discloses a device for fixing a catheter to an arm or other parts of a patient without having to resort to traditional medical adhesive tapes. This prior art device comprises a base part and a part having two grooves which are slightly contracted at the upper part. These grooves may each serve to accommodate a catheter. Further, the base part, which is a rectangular plate shaped part, is provided with an adhesive surface which is protected with a paper film. In use, this paper film is removed and the device is applied to the patient.

This prior art device has the drawback that the device cannot be reused. Once the protective film has been removed and the adhesive surface has been applied to the patient, the position of the device cannot be changed, at least not without a reduction in the adhesiveness of the base plate, thus leading to a less secure fixing of the catheter(s) to the patient. Obviously, reuse of the device is impossible, in particular since sterilization of the device cannot be performed without destructing the adhesive layer on the base plate. Further, the use of adhesive means suffers from the same drawbacks as mentioned in connection with the use of medical tape, e.g. hygienic problems caused by build-up of dust particles, bacteria, micro organisms etc. and the application of the device is difficult in view of the gloves normally used by the medical staff for example when removing the protective paper film. It is also obvious that the device may only be used for tubes having a diameter corresponding to the grooves, i.e. tubes having a size larger than the nominal size cannot be pushed into the grooves, at least not without obstruction the flow in the tube, and tubes having a size only marginally smaller than the nominal size cannot be retained by the grooves. Still further, due to the use of an adhesive as fixing means, the fixing device may unintentionally relatively easily be separated from the patient.

A further example of a prior art device is disclosed in U.S. Pat. No. 6,247,211 B1 that relates to a medical tubing tethering device having a first attachment means in the form of a standard alligator clip with two spring-loaded opposing jaws and a second attachment means in the form of an elongate tether for a medical tube. This tether is in the form of a helical tube that may be wrapped around a medical tube such as a catheter, whereafter the clip at the other end of the tether can be fastened to a piece of clothing on a patient or another article. In this manner the medical tubing will be supported by the tethering device. However, it will be understood that the medical tube will be supported at a distance from the clip and that the fixing thus will be relatively unstable. Further, the fixing of the medical tube by means of a helical tube requires relatively extensive handling since the helical part has to be wrapped around the catheter. Thus, the fixing using this prior art device is relatively time-consuming. Similar applies when the tethering has to be removed again.

Still further, U.S. Pat. No. 5,400,776 relates to a fastener for retaining a medical insufflation tube to the clothing of a patient. This prior art fastener that is made from a flexible polymeric material comprises a first and a second end, where the first end comprises an annular-shaped portion with a circular aperture located therein. An orifice in the annular portion opens into the aperture, whereby a tube portion of a insufflation tube can be compressibly inserted in the aperture. The second end of the fastener comprises a pair of inwardly angled legs. Due to the flexibility of the material the legs are compressed against each other. A lead-in portion of these legs allows the fastener to be applied to a portion of a patient's clothing, i.e. the second end of the fastener is pushed onto the piece of clothing. In this manner a tube can be fixed in relation to the clothing of the patient. However, this fastener has the drawback that it can only accommodate one tube, and the size of the tube has to correspond to the size of the aperture. Further, the clamping function of the first and the second end may interfere with each other. For example, if a tube is inserted in the first end before applying the fastener to the clothing, it may be difficult to press the clothing in between the legs of the second end, in particular if the tube is larger than the intended size and/or if the piece of clothing is relatively thick or coarse. Similarly, it may be difficult to insert a tube in the aperture in the first end if the fastener has initially been applied to a piece of clothing, especially if the piece of clothing is relatively thick or coarse and/or if the tube is larger than the intended size. Thus, it may be time-consuming for the medical staff, nurses, etc. to fix a tube using this prior art fastener. Similarly, the retention effect may prove to be less effective if a tube having a diameter less than the intended size is used and/or if the fastener is fixed to a relatively thin piece of clothing.

BRIEF SUMMARY OF THE INVENTION

The invention provides an improved device for fixing of a line, in particular a line such as a medical tube, wiring for use in the medical field etc.

Further, the invention provides a device, which alleviates the drawbacks mentioned in relation to the prior art technique.

Still further, the invention provides a device that is more flexible and versatile in use than the prior art devices, especially as regards the types and/or sizes of medical lines than may be secured using the invention.

The invention also provides a device that is more flexible as regards the options for placing the device, e.g. on a piece of clothing or another article.

The invention further provides a device that is reusable and that may easily be treated for such reuse, e.g. cleaned, boiled, sterilized etc. between uses.

Further, the invention provides a device that allows the medical line(s) to be placed optimally and that allows the line(s) to be adjusted during use.

Still further, the invention provides a device that is particularly suited for accommodating a plurality of catheters during for example dialysis, where two catheters are used simultaneously.

Also, the invention provides a device that provides an improved securement of the medical line(s) and that provides an improved protection against accidental and/or unintentional shifting and/or removal of a medical line from the device.

Additionally, the invention provides a device that is easy to handle for nurses and other medical staff and that in particular allows a medical line to be inserted in the device with relatively ease, for example also when the user wears gloves and/or in unfavourable conditions, and in particular in such a manner that the use of only one hand is required.

The invention particularly relates to a device for securing a line, said device comprising
- a line retaining part and a base part,
- said line retaining part comprising at least one groove for accommodating a line,
- said groove being designed with flexible retaining means,
- said base part comprising fixing means,
- and wherein said line retaining part and said base part are provided with complementary locking means.

Hereby, a line securing device is provided that is flexible and versatile in use since the groove may accommodate lines such as medical tubes, diagnostic wiring etc. having a diameter within a relatively large range and since the line retaining part is designed to be connected to a separate base part. Thus, the base part may be designed specifically to be fixed to certain articles, e.g. a piece of clothing, a part of a piece of medical equipment etc., and further, different base parts may be provided, each being designed for being fixed in different manners, whereby a hitherto unseen flexibility and versatility is provided. Further, it is achieved that the device may be located easily and that the location or position may be easily adjusted during use.

Preferably, said flexible retaining means of said retaining part may comprise a plurality of protruding flexible parts placed essentially lateral of the groove.

Hereby, it is achieved that a line may be securely withheld in the groove even when the diameter of the line is considerably smaller than the width of the groove.

Advantageously, said protruding flexible parts may be designed as blades that protrude into the groove.

Hereby, an advantageous design is provided that allows the flexible means to apply an efficient pressure to the line in the groove and that still allows the line to be inserted in the groove in a relatively effortless manner.

In a preferred embodiment, said protruding flexible blades may be located at an angle in relation to an axis of the groove.

Hereby it is achieved that the line may be further secured from being pulled out of the securing device in the longitudinal direction of the line, since the blades will provide a firmer grip when the line is pulled in the opposite direction of the blades. This may be particularly advantageous for example when the securing device is used to fix a line, e.g. a catheter, near the place where e.g. a catheter needle punctures the skin and is entered in e.g. a vein or an artery. Here, it is particularly important that the line is prohibited from being moved accidentally, i.e. since the needle or needles might be pulled out of the skin, which might have immense consequences. According to this embodiment, the line retaining part may be placed in such a manner that the angled blades will prevent that the catheter is accidentally pulled away, e.g. by having the blades point in the direction towards the e.g. needle.

Further, this embodiment has the advantage that the insertion of a line in the groove may be performed with relatively ease and by using for example only two fingers when the line is inserted from the end of the groove where the blades are angled away, i.e. into the groove. It will be understood that the line thus will "follow" the direction of the blades and that only a small pressure that will be sufficient to cause the blades to slide towards the sides of the groove need to be applied. Thus, the line may be inserted by placing the line above the groove, applying force downwards by e.g. a thumb starting at one end of the groove and working towards the other end, while the device may be supported by e.g. the index finger.

Advantageously, said angle of the flexible blades in relation to the axis of the groove may be located in an interval of 10°-80°, in a more preferred form 25°-60°, in a still more preferred form 40°-50°, and in particular at an angle of 45°.

In a particular embodiment, said flexible retaining means, e.g. said plurality of protruding flexible parts, may be placed only at one side of the groove.

Hereby a device is provided that may be designed in a relatively simple manner that may be easier to manufacture and thus may be advantageous from an economic view while simultaneously providing the abovementioned advantages.

Preferably, said flexible retaining means, e.g. said plurality of protruding flexible parts, may be placed at both sides of the groove.

Hereby a device is provided that may be designed to accommodate a considerable range of lines as regards e.g. the diameter of the lines, and that still will provide a secure fixing of the lines.

In a further particular embodiment, said line retaining part may comprise only one groove for accommodating a line.

Hereby an embodiment is provided that may be preferable in many circumstances where only one line, e.g. a catheter is used, for example when blood transfusion is concerned, since e.g. the device may be smaller in size, thus more economic to manufacture and less obtrusive and easier to place at or on the patient.

Advantageously, said retaining part may comprise at least two grooves for accommodating a line each, said grooves preferably being placed essentially in parallel.

Such an embodiment may provide a versatile device that may be used in numerous applications, e.g. also where only one line is used, but in particular it is advantageous in applications where two lines are always needed, e.g. for example in connection with dialysis.

Preferably, said line retaining part may be made of a polymeric material.

Hereby, the line retaining part may be manufactured in a material that facilitates the necessary flexibility and other characteristics that are desired, e.g. the ability to withstand the high temperatures necessary in order to e.g. sterilize the line retaining part between uses, and that further facilitates cost efficient manufacturing of the line retaining part. Such materials may for example be polypropylene (PP), for example glass fiber reinforced polypropylene, or other suitable plastic materials and polymers.

It should be mentioned that in order to provide additional security against an accidental release of a line, the flexible parts, e.g. the flexible blades may be designed in such a manner that at least part of the surface that may contact the line, may comprise friction enhancing means. For example, the surface may comprise a rough surface, small irregularities etc., or the surface may comprise a layer of friction enhancing material such as for example rubber or a similar material. Similar applies to the bottom of the grooves, where at least part of the surface, e.g. the bottom support may be designed in similar manner, e.g. with a rough surface, small irregularities etc., or with a layer of friction enhancing material such as for example rubber or a similar material, in order to achieve that the line will resist sliding in the groove.

According to an advantageous embodiment, said complementary locking means of said line retaining part and said base part may comprise snap locking means.

Hereby, a device is provided whereby the two parts may easily be connected to each other, even when the person, e.g. the nurse is wearing gloves, which is normally the case in such medical situations where the device is used. It will be understood that in most cases the two parts will be provided in connected form, e.g. ready for use, but as already explained, it may be preferable to use a different base part for a device, in which case it will be relatively easy to disconnect two parts and connect a different base part to the line retaining part. Further, it may be preferable to disconnect the parts when cleaning, boiling and/or sterilizing the device between uses. Further, the snap connecting means are also advantageous in view of economic optimal manufacturing of the parts, and finally the snap connecting parts will give a secure connection of the two parts.

Preferably, said snap locking means may comprise a tap placed on said base part and a cavity in the line retaining part or vice versa.

Hereby, the snap locking means may be designed in an advantageous manner, in particular when the cavity is placed in the line retaining part, since this part will normally have a size allowing a cavity to be incorporated in the body.

Advantageously, said tap may comprise a protruding annular part and that said cavity comprises a complementary annular groove or vice versa.

In this manner the parts may readily interact and snap together when the parts are engaged, and further these means may be manufactured using readily available techniques, e.g. when using moulding etc.

According to a further advantageous embodiment, said complementary locking means of said line retaining part and said base part may be designed as a swivel joint, allowing the line retaining part to be adjusted in relation to said base part.

Hereby, it is achieved that the line retaining groove or grooves may be directed in a suitable direction, e.g. suitable in view of the comfort of the patient and the requirement that the lines may not be restricted, even though the device as such is located in a less than optimal direction, since the line retaining part may easily be turned in the desired direction, either by hand or automatically caused by e.g. the stiffness of the tube or tubes.

Preferably, said line retaining part and said base part may be designed with limit stops for said swivel joint, allowing the line retaining part to be adjusted within a limited angular range in relation to said base part.

Hereby, the swivel range may be limited to a preferable range, e.g. 180°, whereby it is achieved that the flexible blades will always be directed in the most preferable direction, e.g. in order to hold a line against a potential pulling force. It will be understood that, according to some embodiments and if needed, the line retaining part may be disconnected from the base part, turned e.g. 180°, and connected again if a swivel range in the other direction is preferred.

According to a further advantageous embodiment, said line retaining part and said base part may be designed with interacting means, e.g. teeth, a toothed ring, cogging or similar means, that allows a relative movement and facilitate a parking of the line retaining part at certain angles in relation to said base part.

Hereby it is achieved that the two parts may be turned, e.g. adjusted, relatively easily in relation to each other by hand and left in a desired position where the parts will remain because of the interacting means.

Advantageously, said fixing means of said base part may comprise two opposing jaw parts that are forced together by spring means.

Hereby, the base part may be clamped to a piece of clothing, a piece of textile etc. or another article at or near the patient.

According to a further advantageous embodiment, said spring means may comprise a flexible connecting part between the two jaw parts.

Hereby, it is achieved that the spring means of the base part may be manufactured as an integrated part, where the part between the two parts will serve not only to connect these two parts but also to provide a spring force.

Further, said spring means may comprise a flexible spring part connected to one of the two jaw parts and acting on the other jaw part.

Hereby, further spring force for the clamping jaws may be provided in a manner that still allows for a relatively easy manufacturing of the base part, e.g. as a moulded part, where the flexible spring part is moulded as an integral part.

Preferably, said fixing means of said base part may comprise hinge means comprising hinge parts on both jaw parts.

Hereby, a further advantageous embodiment is provided, whereby the base part may be designed as a clamp or clip, i.e. with hinges, in a manner that still allows for a relatively easy manufacturing of the base part, e.g. as a moulded part, where the hinge parts may be moulded as integral parts.

According to a particular advantageous embodiment, said hinge parts on the jaw parts are designed as a hook or latch element formed on one of the jaws and a corresponding opening formed on the other jaw.

Hereby it is achieved that the base part may be manufactured with only few parts separate parts and preferably only one part, since the main part needs only be bent in such a manner that the jaw parts are abutting, whereby the hook or latch on one jaw part will engage with the opening formed in the other jaw part, whereafter the hinge parts will be latched together, and the clip or clamp will be ready for use.

According to a further advantageous embodiment, said base part may be formed as a flexible elongated part, each end forming a jaw part and an intermediate part forming a flexible part.

Hereby, it is achieved that the base part may be manufactured as—preferably—a single integrated part, where the part between the two parts will serve not only to connect these two parts but also to provide a spring force and whereby the base part may be readily assembled to form a clamping part.

Preferably, said base part may be made of a polymeric material.

Hereby, the base part may be manufactured in a material that facilitates the necessary flexibility and other characteristics that are desired, e.g. the ability to withstand the high temperatures necessary in order to e.g. sterilize the base part between uses, and that further facilitates cost efficient manufacturing of the base part. Such materials may for example be polypropylene (PP), for example glass fiber reinforced polypropylene, or other suitable plastic materials and polymers.

According to a further advantageous embodiment, said fixing means of said base part may comprise spring-loaded or flexible means that may be clipped onto structural parts.

Hereby it is achieved that the device according to the invention may be used in numerous applications, e.g. where the device may be clipped onto rods, tubes and other elements that form part of equipment near the patient, e.g. furniture, beds, supports for medical equipment, etc. as well as head bands, head sets, ear sets, ear clips or other parts worn by the patient, etc.

According to a still further advantageous embodiment, said fixing means of said base part may comprises adhesive means that may be applied onto structural parts or other articles.

Hereby, a device is provide where the line retaining part according to the invention may be reusable and may be used in connection with a base part that may be designed as a disposable and relatively cheap part, i.e. using an adhesive part, while still providing the other benefits mentioned above, e.g. the ability to adjust the angle between base part and line retaining part etc.

According to a still further advantageous embodiment, said fixing means of said base part may comprise mechanical means for securing the base part to an item at, on or near the patient. Hereby, the base part may for example be or comprise an arm band, strap or similar means, a head band, an ear clip, a head or ear set, a belt etc etc.

It is noted that it will be understood that the base part and the line retaining part may comprise other connection means than explicitly mentioned, for example magnetic means, etc.

According to a particular advantageous embodiment, said line retaining part may comprise connection means on a side part for mechanically connecting said retaining part to a further retaining part.

Hereby it is achieved that a line retaining part comprising more grooves than the standard part may readily be provided using the standard retaining parts and using a standard base part.

Advantageously, said connection means on a side part may comprise first connection means on a first side part and second connection means on a second side part, said first and second connection means being complementary.

Hereby it is achieved that a line retaining part comprising a specific, desired number of grooves, e.g. 2, 3, 4, 5, 6, etc., may readily be provided using the standard retaining parts and using a standard base part.

Preferably, said first and second connection means may be designed as dovetail joints.

Hereby the connection means may be designed in a manner that provides a firm and stable connection while still allowing the parts to be manufactured in an economical optimal manner, e.g. as mouldings etc. whereby the device may still be manufactured cost-efficiently.

According to a still further advantageous embodiment, said line retaining part may comprise a side part that is designed in order to form a part of said complementary locking means when said line retaining part is connected with a similar or identical line retaining part.

Hereby it is achieved that a line retaining part that is formed as a connection of two or more standard parts, may be placed in a balanced manner on a base part, e.g. the locking tap on the base part may be connected to a locking cavity on the combined line retaining part that is placed near the middle of the combined line retaining part.

According to a further preferable embodiment, said line retaining part may comprise further means for withholding a line in said groove.

Hereby an additional security is achieved against an accidental release of the line in the groove, for example if the line should be forced upwards. Such means may for example be pointed upper edges on the blades, parts placed above the groove(s) etc.

Advantageously, said further means for withholding a line in said groove may comprise a lid part that may be connected to the line retaining part by a hinge.

Hereby an additional security is achieved against an accidental release of the line in the groove, for example if the line should be forced upwards, which additional security may be achieved with few and simple means that will only increase the cost infinitesimally and will not reduce the user-friendliness of the device.

Finally, the invention pertains to a uses of a device as generally described above in accordance with the invention in connection with dialysis, blood transfusion, chemotherapy, insufflation, emergency treatment and/or intensive care treatment, but it will be understood that the device according to the invention may find use in a wide range of applications.

BRIEF DESCRIPTION OF THE FIGURES

The invention will be explained in further detail below with reference to the figures of which FIG. 1a shows a line retaining part according to a first embodiment of the invention, seen in a perspective view, FIG. 1b is a perspective view from the rear of a similar line retaining part, FIG. 2a shows a line retaining part as shown in FIG. 1a seen from above, FIG. 3 shows a second embodiment of a device according to the invention seen in a perspective view.

DETAILED DESCRIPTION OF THE INVENTION

Figure 2B:
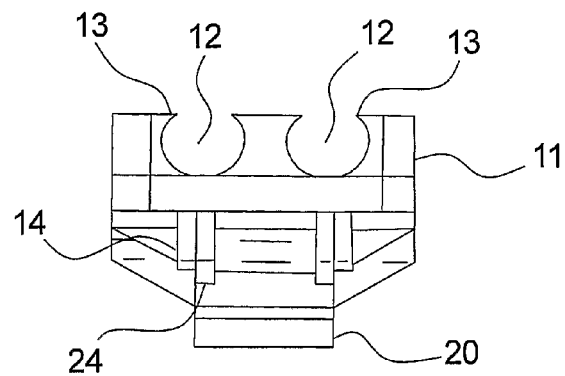
FIG. 2b shows a line securing device with a line retaining part as shown in FIG. 1a seen from the rear.

In FIGS. 1a to 2d a first embodiment of a securing device 10 according to the invention is shown. These drawings as well as the rest of the drawings are for illustrative purposes only and the actual size of the device as well as the proportions may differ from the illustrations of the drawings, which will be obvious. The securing device is generally designated 10 and comprises a line retaining part 11 and a base part 20. The line retaining part 10 comprises two line retaining grooves 12 in the embodiment shown, but it is noted that the line retaining part 10 may comprise only one such groove 12 and that it may comprise more than two grooves, e.g. three, four, five or more. As it will be explained in detail further on, such a groove 12 may serve to hold or retain elongated elements such as lines in the form of tubes, catheters, wires etc. that may be used in different applications in particular in the medical field. The groove or grooves are adapted for releasably holding lines with predefined dimensions but further the grooves are provided with flexible means 13, e.g. elastic means for accommodating lines with a certain dimensional span in such a manner that the line or the lines are held securely and in such a manner that a line may easily be inserted in a groove 12. These flexible means will be described in further detail in the following but as illustrated they may comprise parts protruding into the groove, for example placed at an upper part of the groove or at a lower part. Such protruding parts may be made of elastomers, rubber material, polymers, plastic materials etc. As shown in FIGS. 1a to 2b the grooves 13 may be designed with an essentially circular section, but with an opening upwards, but it will be obvious that other forms may be used as well.

Further, in FIGS. 1a to 2d it is shown that the retaining part 11 may comprise a flat rear part 16 that may serve to support the line when it is placed in the groove 12. Further, this rear part 16 may also serve as support for the user when a line is inserted in the groove.

Figure 2C:
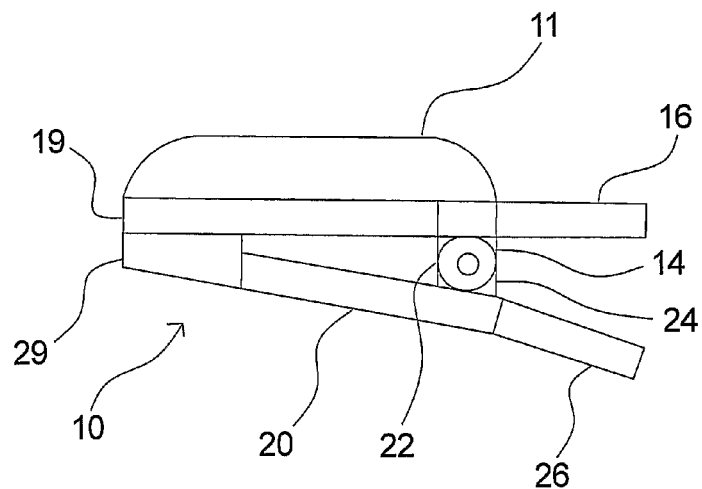
FIG. 2c is a side view of the line securing device shown in FIG. 2b.
Figure 2D:
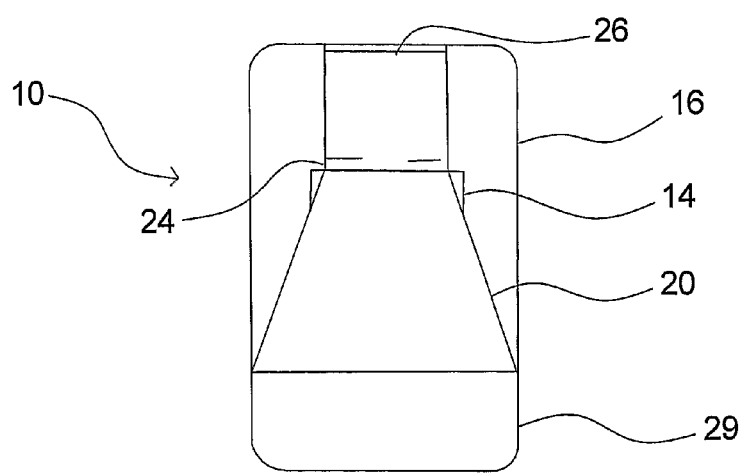
FIG. 2d is a view from below of the line securing device shown in FIG. 2b.

The line retaining part 12 also comprises a hinge part 14 that may cooperate with a hinge part 24 on the base part 20 as shown in FIG. 2c, whereby the line retaining part 11 and the base part 20 together form a clip or clamp with a jaw 19 on the line retaining part 11 and a jaw 29 on the base part 20. A spring 22, for example a coil spring, a torsion spring etc. are placed in connection with the hinge parts as indicated but other means of providing a clamping force may be used as well, e.g. a spring element placed between the line retaining part 11 and the base part 20. As shown in FIGS. 2b-2d, the base part 20 comprises a rear part 26 that may serve as a finger grip, whereby a user may grip the device 10 by the rear part 16 and the finger grip 26 and press these together, thus opening a gap between the jaws 19 and 29, and placing the securing device 10 at an appropriate location using the clamping force of the jaws, for example on a piece of clothing or another article in the vicinity of the patient.

Instead of using clamping means for locating the securing device 10 the base part 20 may be designed for being fixed to the patient or to an article in other suitable manners, which will be described later on in detail in connection with further embodiments of the invention.

In FIG. 3 a second embodiment of a securing device 50 according to the invention is illustrated. In general this embodiment is designed in correspondence with the first embodiment, i.e. with a line retaining part 60 and a base part 80. In the following these parts will be described in further detail with reference to FIGS. 3 to 22b.

The line retaining part 60 comprises in the shown embodiment two grooves 62 for accommodating a line each. These two grooves 62 are separated by a centre beam 61 that forms a structural main part of the part 60 that may be manufactured by injection moulding or by other suitable processes, e.g. moulding processes. Each groove 62 is open upwards and may also be open downwards, even though in the shown form a bottom support 68 is placed at the bottom, e.g. for supporting the line in the groove and/or for providing structural strength for the line retaining part 60. Each of the grooves 62 comprises flexible retaining means in the form of flexible blades 63 that in the illustrated example are placed at each side of each groove 62. As shown, these blades 63 are oriented with an angle in relation to the axis of the grooves 62. The angle a (FIG. 6) may, in consideration of particular applications, lines etc. be defined to have a value in a wide range, e.g. in an interval of 10°-80°, in a more preferred form 25°-60° or in a further preferred form 40°-50°. In many applications, an angle of approximately 45° as indicated in the drawings is found preferable.

The blades 63 may be placed at each side of the groove 62 as shown in the drawings but obviously the flexible blades 63 may be located at only one side of each groove 63. Further, as shown, a plurality of blades 63, in the illustrated example four, may be used at each side. Obviously, fewer than four may be arranged, e.g. one, two or three, and more than four may also be arranged, e.g. five, six, seven etc. It is noted that the flexible blades 63 are angled in the same direction, which is preferable as explained further on. Further, it is noted that the flexible blades are placed opposite each other with a certain offset as shown in e.g. FIG. 6, where it is indicated that the tips or edges of the flexible blades are arranged in such a manner that the tip of one blade at one side of the groove 63 is placed intermediate two opposing tips of blades located at the other side. Such a configuration is preferable in terms of flexibly withholding a line in the groove. Though, it will be understood that the tips of the blades 63 may be located opposite each other, i.e. without an offset, in certain applications.

Figure 6:
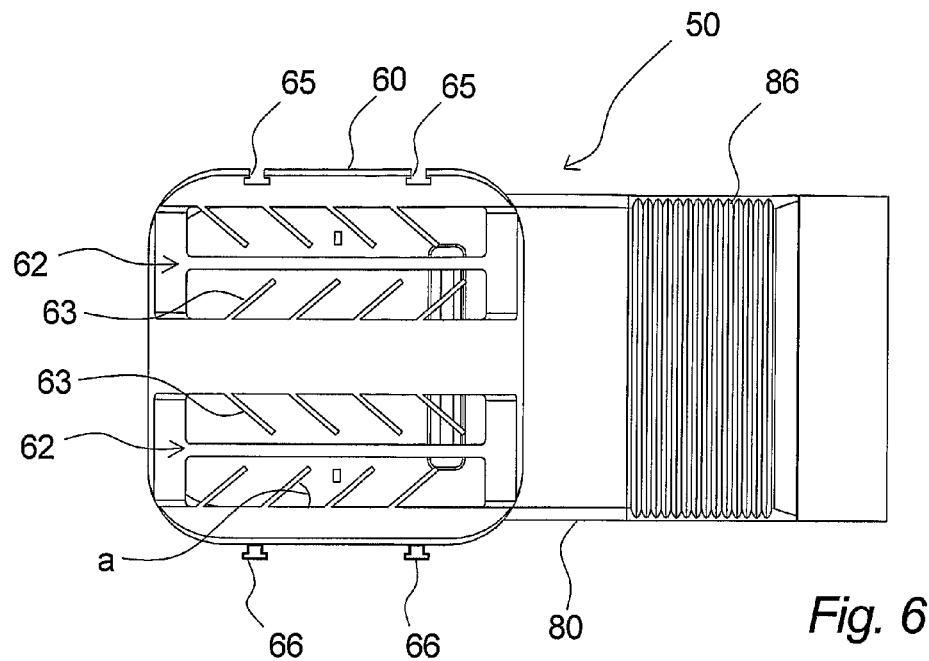
FIG. 6 is a view from above of the device shown in FIGS. 3 and 4.
Figure 7:
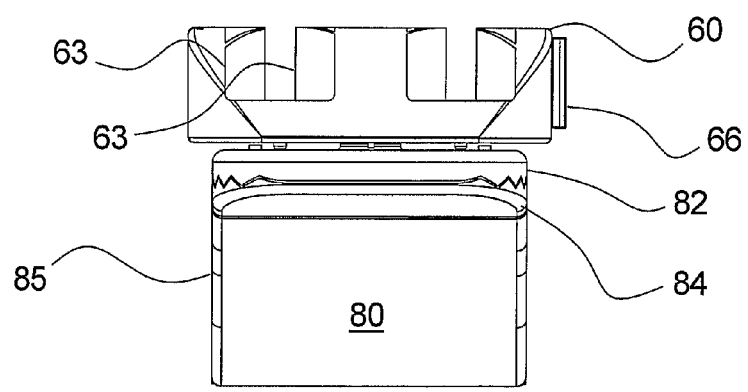
FIG. 7 is a front view of the device shown in FIGS. 3 and 4.
Figure 8:
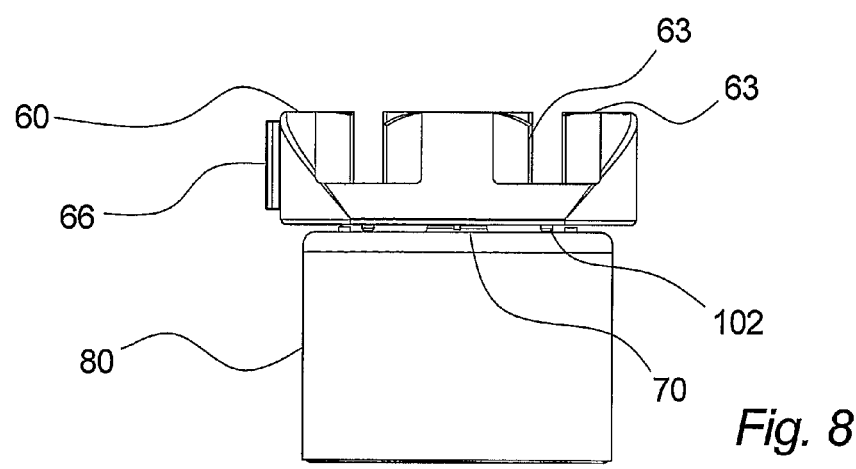
FIG. 8 is a rear view of the device shown in FIGS. 3 and 4.

Since the flexible blades 63 occupy a large part of the groove 62, cf. e.g. FIG. 6, it will be understood that lines having a small diameter in relation to the width of the groove may be retained by the blades. Similarly, it will be understood that lines having a diameter corresponding to the width of the groove (or nearly the width of the groove) may be accommodated in the groove, since the blades will flexibly be moved towards the sides of the groove 62. Thus, lines with a diameter within a large range can be secured by the device 50. Further, it will be understood that because of the angled or slanted position of the flexible blades, a line accommodated in the groove 62 will be held particularly firm in one direction since a pull in the line in a direction against the blades 63 will be counteracted by the blades, e.g. the blades will provide a firmer grip in consequence of the pull, whereas a pull in the other direction will be counteracted only by the flexible grip of the blades.

It will also be understood that because of the angled position of the blades 63, a line can be easily inserted in the groove 63 if it is placed on top of the groove, e.g. supported on the top of the blades 63, and pushed into the groove starting at the end where the blades are angled into the groove, e.g. the end of the groove 62 at the top left side of FIG. 3, and working towards the other end. Hereby, the line will ease the blades 63 towards the sides of the grooves, thus facilitating an easy insertion of the line as it is pushed downwards, for example using a thumb.

Figure 3A:
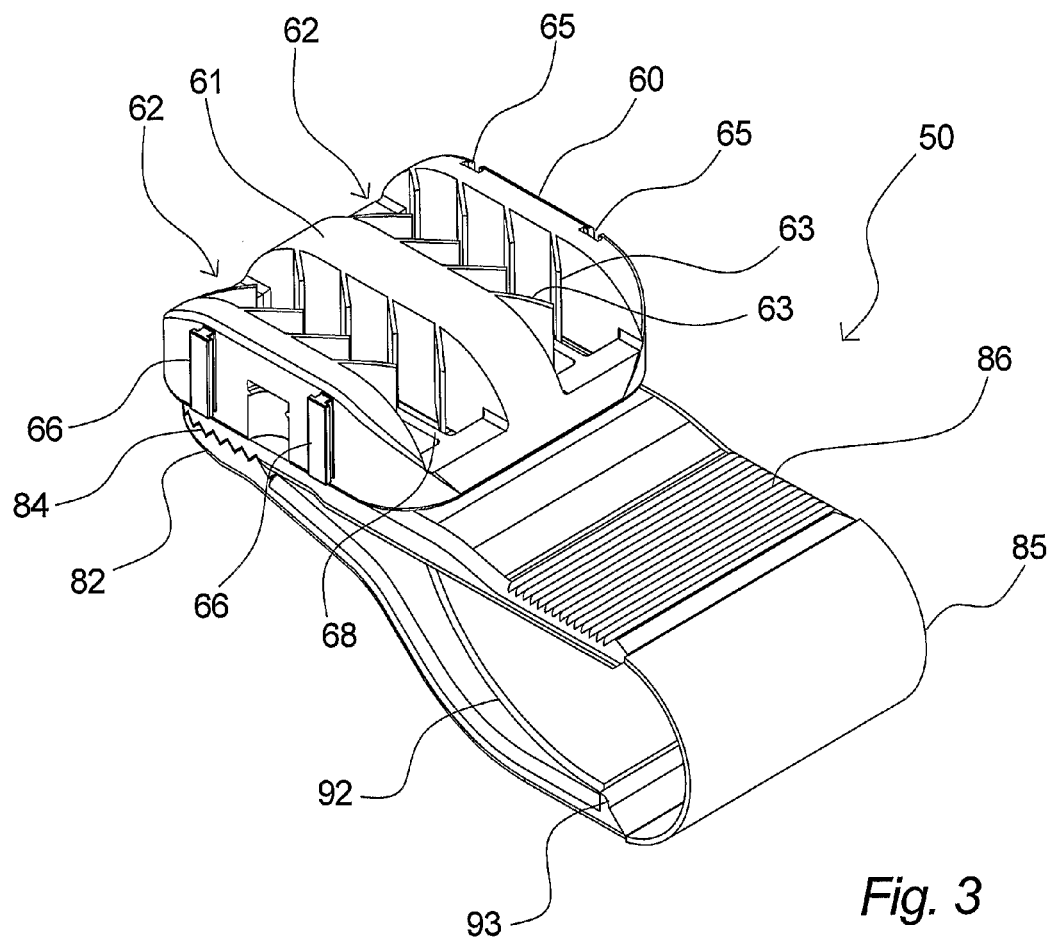
FIGS. 3a-3c show different embodiments of flexible blades.
Figure 3A:
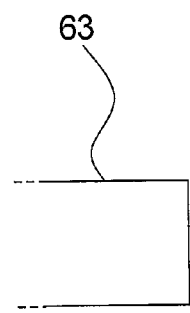
Figure 3B:
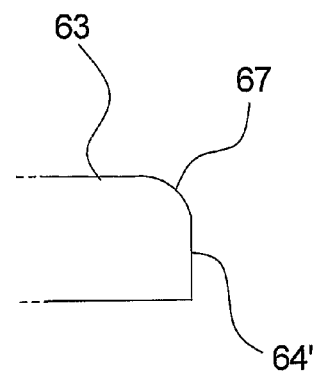
Figure 3C:
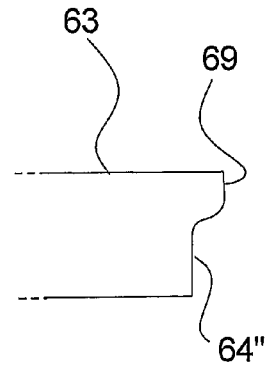
Figure 4:
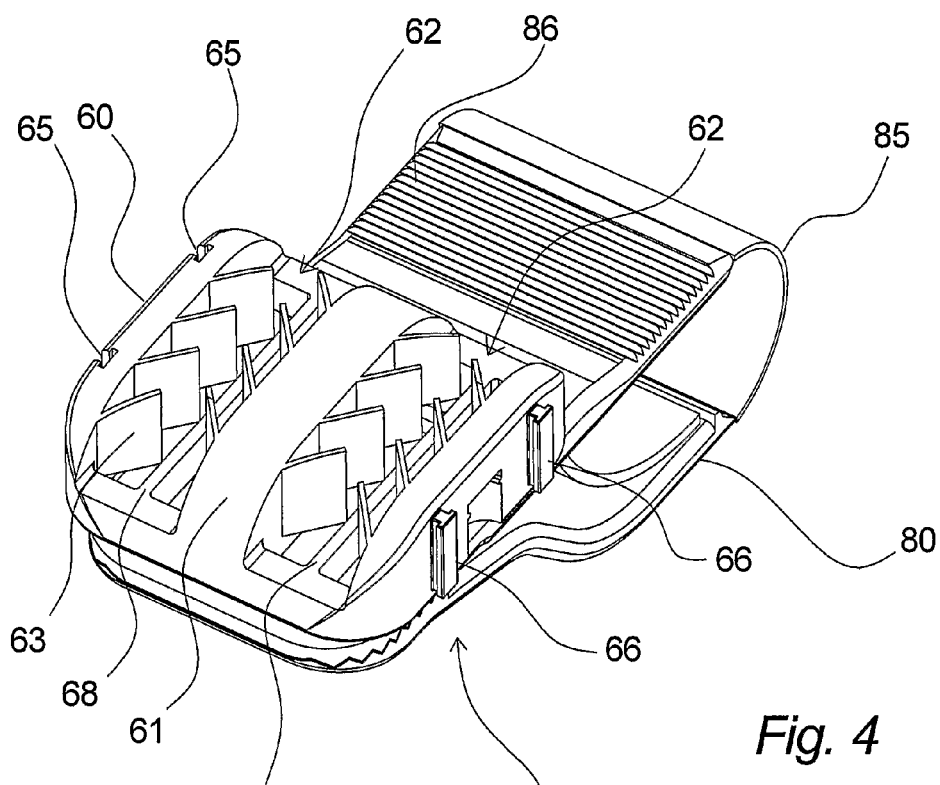
FIG. 4 shows the second embodiment of the device also in a perspective view, but seen from another angle.
Figure 5:
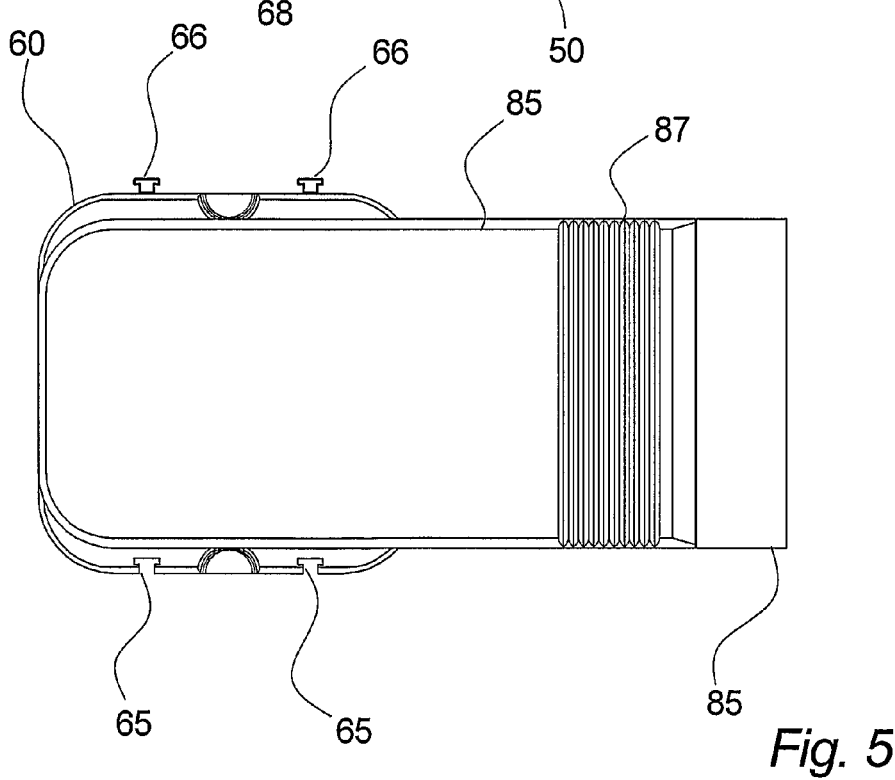
FIG. 5 is a view from below of the device shown in FIGS. 3 and 4.

As shown, the flexible blades 63 may be configured as square plates that may be moulded as integrated parts of the line retaining part 60. Such forms are shown in FIGS. 3a to 3c, where a flexible blade is shown on a larger scale. In FIG. 3a, the blade 63 is shown with a rectilinear edge 64. Instead, as shown in FIG. 3b, the edge 64' may be formed with a rounded upper edge 67, which may further facilitate an easy introduction of a line in the groove. A further example of the form of a blade is shown in FIG. 3c, where the edge 64" is provided with an overhanging edge part 69 that may serve to apply further pressure to a line having a relatively large diameter, but will also serve to provide a firmer hold of a line with a relatively small diameter, since the edge part 69 will be placed above the line when it has been inserted in the groove. It will be understood that combinations of the forms shown in FIGS. 3a to 3c are possible and that other forms may be used as well.

According to a further embodiment that is not illustrated in the drawings, a lid part may be placed above (part of) the groove 62 and/or above (part of) the line retaining part 60 after the line or lines have been inserted in the grooves in order to further secure the lines. Such a lid part may be hinged to the line retaining part or may be a separate part.

As also shown in FIG. 3, the line retaining part 60 is provided with means for connecting the part 60 to other parts, in particular similar retaining parts. Such means may as shown be a dovetail groove 65 placed at one side of the line retaining part 60 and a corresponding dovetail 66 placed at the other side. In this manner, two or more line retaining parts may be connected firmly together to form a line retaining part having a desired number of grooves 62. It will be understood that the width of the dovetail parts may decrease downwards in order to align the parts in the vertical direction, or the dovetail groove 65 may be provided with a stop at the bottom. As illustrated, two dovetail grooves 65 and two dovetails 66 may be provided in a line retaining part, but obviously only one or more than two of these may be present. Alternatively, other means of locking two or more line retaining parts together may find use, e.g. snap locking means etc.

As further shown in FIG. 3, the securing device comprises a base part 80, cf. e.g. FIGS. 4 to 8, that is in the form of a clamping device.

This base part will be described in further detail with reference to FIGS. 14 to 19.

Figure 14:
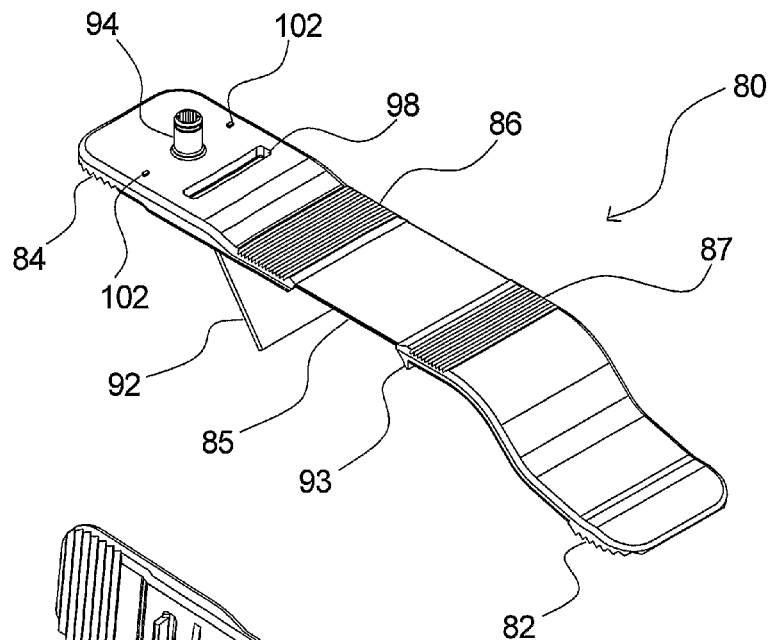
FIG. 14 is a perspective view of base part in the form of a spring clip device seen in unfolded form, e.g. before the base part is made active.
Figure 15:
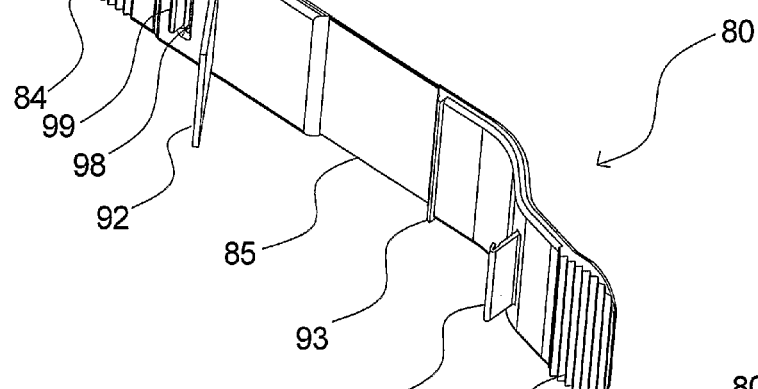
FIG. 15 is a perspective view of the base part shown in FIG. 14, but seen from another position.
Figure 16:
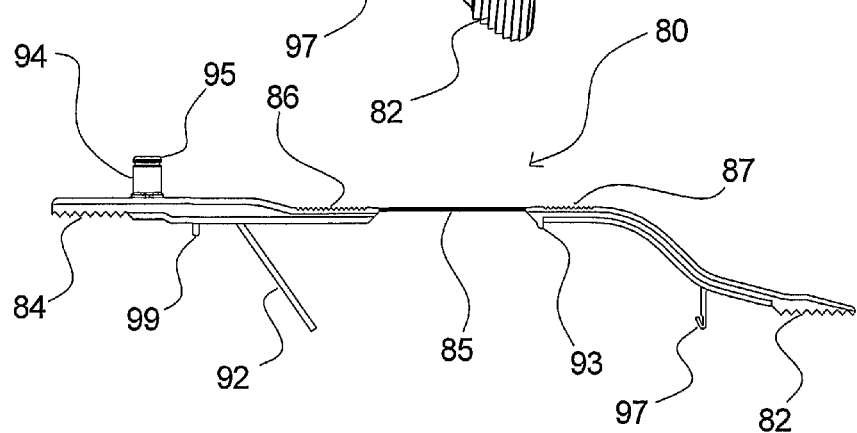
FIG. 16 is a side view of a base part similar to the embodiment shown in FIGS. 14 and 15.
Figure 17:
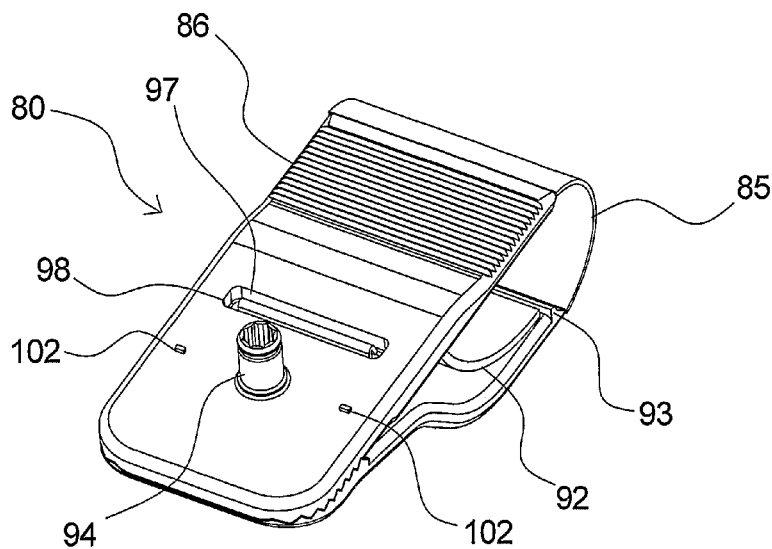
FIG. 17 is a perspective view of a base part similar to the embodiment shown in FIGS. 14 and 15 in folded form, e.g. in active form and ready to be connected to a line retaining part.

The base part 80 shown in FIGS. 14 and 15 is preferably manufactured as a one piece item by e.g. injection moulding or the like. The part 80 comprises an elongated body having an intermediate part 85 and two end parts that form gripping jaws 82 and 84. Further, near the intermediate part 85 the base part 80 is provided with finger grips 86 and 87 on the upper side, and near one end the base part 80 is provided with a snap locking part 94 and limit stops 102, the function of which will be described later on. Further, at this end the base part 80 is provided with an opening 98 and on the other side a hinge abutment 99 is placed as shown in FIGS. 15 and 16. Further, a flexible spring part 92 is located in the vicinity of these parts as shown. Finally, at the other end a stop 93 for the spring part 92 is located, and further a hinge latch 97 is placed here.

Figure 18:
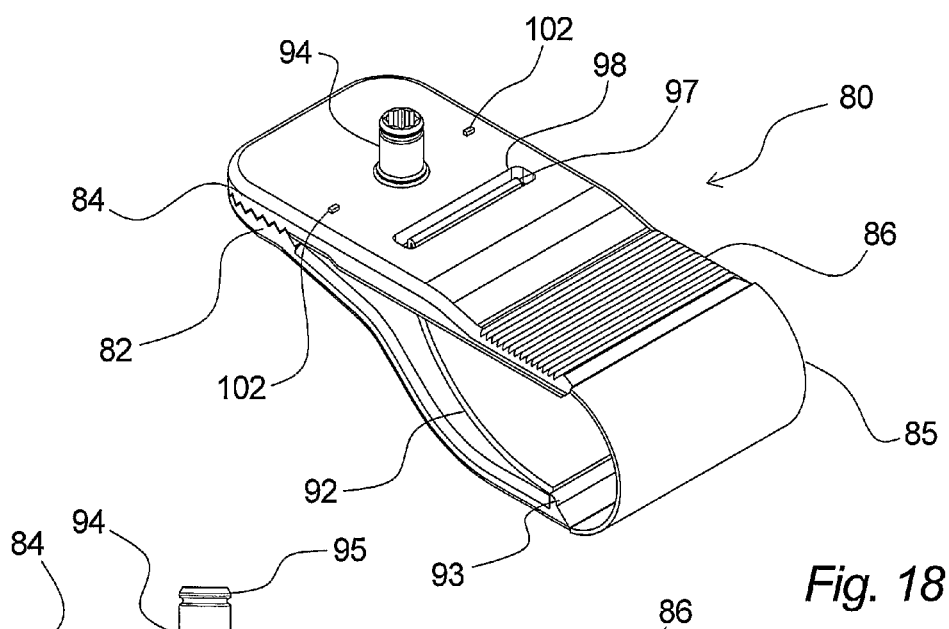
FIG. 18 is a perspective view of the base part shown in FIG. 17, but seen from another position.
Figure 19:
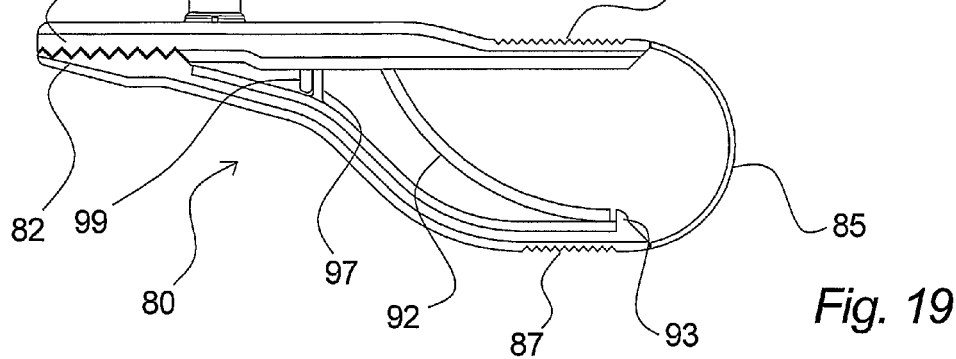
FIG. 19 is a side view of the base part shown in FIG. 17.
Figure 20:
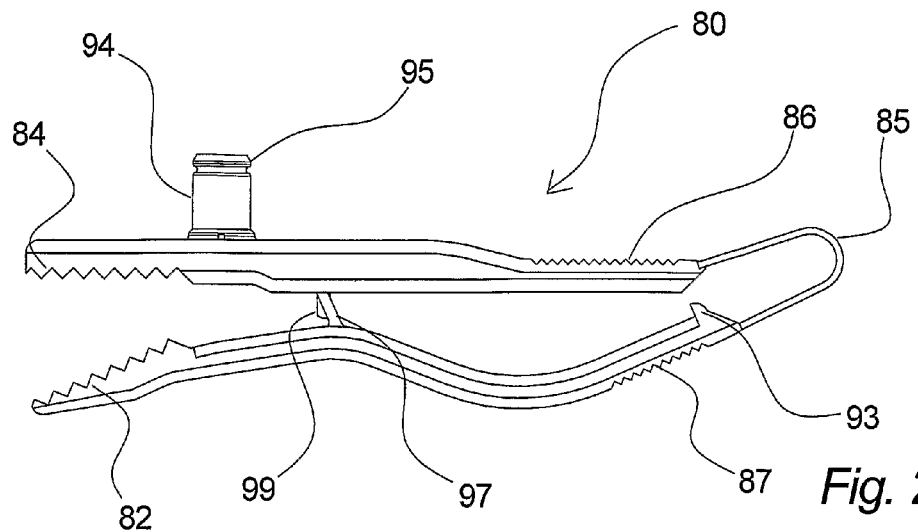
FIG. 20 is a side view of the base part corresponding to FIG. 19, but with the jaws of the clip opened.
Figure 21:
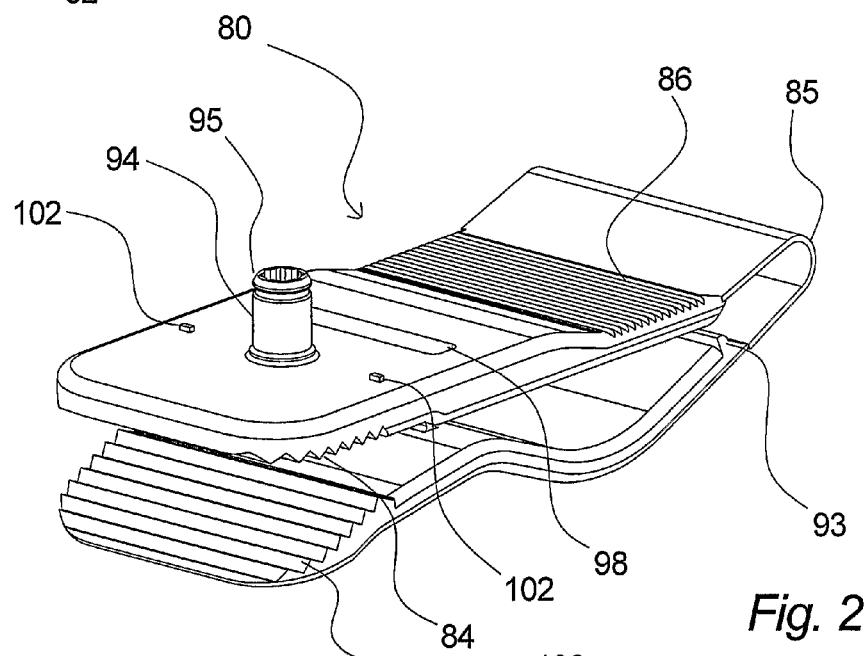
FIG. 21 is a perspective view of the base part shown in FIGS. 17-20 with the jaws of the clip opened.

The interaction of these parts will be further explained with reference to FIGS. 16 to 19. The two ends of the base part 80, e.g. 82 and 84, are brought together, e.g. the gripping jaw 82 is brought up towards the gripping jaw 84. During this motion, the intermediate part 85 will bend flexibly and elastically, since it is designed with smaller dimension(s) than the neighbouring parts, and the part will end up as shown in FIG. 19. The flexible spring part 92 will abut against the stop 93, and the hinge latch 97 will be led or forced, e.g. snap through the opening 98, until the hinge abutment 99 prevents further motion. In this situation the hook on the end of the hinge latch 97 will grip the edge of the opening 98 as indicated in FIG. 18, preventing the parts from being separated again.

Thus, as shown in FIG. 19, the gripping jaws 82 and 84 will be pressed together, forced by the flexibility of the intermediate part 85 and the spring part 92. As shown, the finger grips 86 and 87 are located on opposing parts, and when a compression force is applied to these two grips, for example by means of two fingers, the jaws 82 and 84 will open, since the parts will swivel at the hinge parts 97, 98 and 99. This is shown for example in FIGS. 20 and 21, where, although, a spring part 92 is not shown. It will be understood that since the intermediate part 85 provides flexibility, this part may serve to provide spring force alone, but preferably a separate further spring part may be provided, e.g. 92 as shown in e.g. FIGS. 17 to 19.

The gripping jaws 82 and 84 are as shown provided with teeth in order to allow the jaws to provide a firm grip on e.g. a piece of clothing. Further, or instead, the inner surface of the gripping jaws 82 and 84 may comprise other means to provide a secure gripping or clamping function, e.g. friction enhancing means such as for example a layer of rubber or other materials having a high coefficient of friction.

As shown in e.g. FIGS. 14, 17, 18 and 20, the finger grips 86 and 87 are provided with ribs in order to allow a user to manipulate the device with ease, even with gloves, and in order to prevent that the clamp slips out of the fingers of the user. Instead of ribs or in addition to these the finger grips 86 and 87 may also comprise friction enhancing means such as for example a layer of rubber or other materials having a high coefficient of friction.

As mentioned above, the base part 80 is provided with a snap locking tap 94 as shown in e.g. FIGS. 16 and 18. This serves to provide connection to the line retaining part 60 as shown in e.g. FIGS. 9 and 10. As indicated in FIG. 16, the snap locking tap 94 is essentially cylindrical with a protruding annular part 95 that may be provided by having an annular groove in the tap 94 below the annular part 95. Correspondingly, the line retaining part 60 comprises a snap locking cavity 70 as shown in e.g. FIG. 11. This snap locking cavity 70, that may be essentially cylindrical, comprises an annular groove 71 and an annular rib 72, where the annular groove 71 corresponds to the protruding part 95 on the snap locking tap. Thus, when a line retaining part 60 is connected with a base part 80, the snap locking tap 94 is inserted in the snap locking cavity 70, until the annular protruding part 95 engages with the annular groove 71, whereby a connection is established. This connection is a swivel connection, allowing the line retaining part to turn in relation to the base part. However, in order to limit this movement, limit stops may be provided as shown in e.g. FIGS. 8, 11, 17 and 18. On the upper side of the base part two limit stops 102 are located and similarly limit stops 102 may be located at the underside of the line retaining part 60 as shown on e.g. FIG. 12. In this manner, the movement may be limited to a plus/minus 90° movement or whatever angle is found appropriate.

Figure 9:
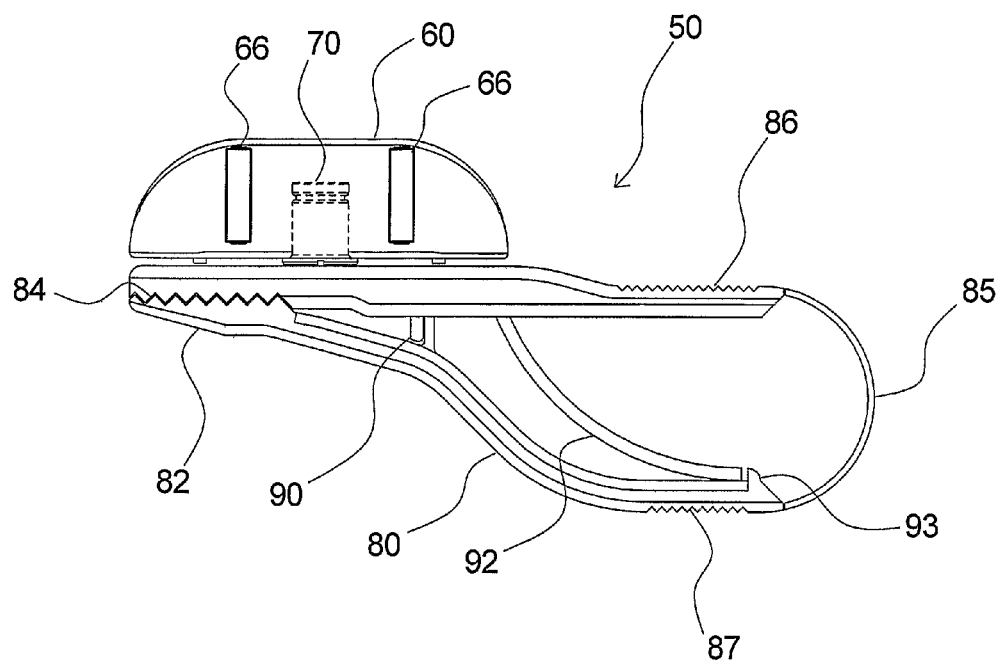
FIG. 9 is a side view of the device shown in FIGS. 3 and 4.

Further, as shown in FIG. 9, these limit stops 102 and in particular a slide element 101 (cf. e.g. FIG. 12) may also serve as distance blocks between the base part and the line retaining part, e.g. in order to reduce friction between these parts and allow an effortless rotational movement. Also, a distance ring 104 may be provided at the underside of the line retaining part 60 as shown on e.g. FIG. 11 or alternatively as a part on the upper side of the base part 80, e.g. as a part of the snap locking tap 94, cf. e.g. FIGS. 17 to 21, in order to facilitate the swivel action.

Further, the two parts, e.g. the line retaining part 60 and the base part 80, may comprise means (not shown in the figures) on the abutting surfaces that facilitate that the parts may remain in a certain relative position. Such means may be friction surfaces, but also one or both or the parts may be provided with toothed means, e.g. a toothed ring on one part and one or more teeth on the other part, that engages with each other in such a manner, that the two parts may be turned by hand until the desired angle is found, whereafter the two parts will be locked to each other in this position.

Figure 10:
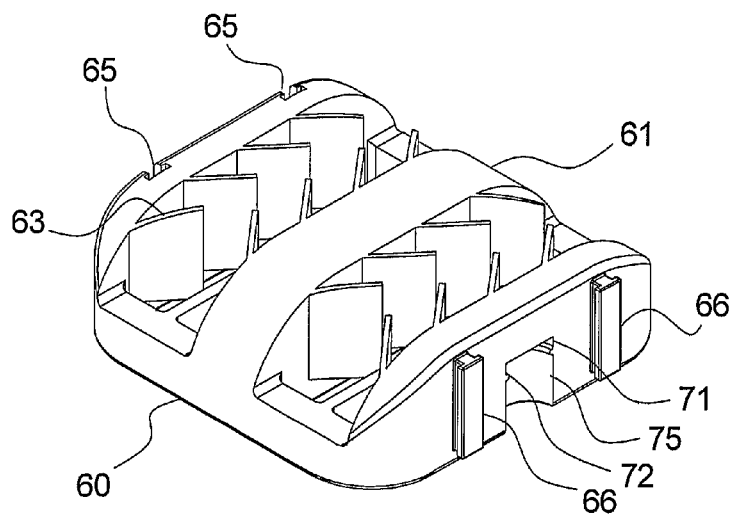
FIG. 10 is a perspective view of a line retaining part according to the second embodiment of the invention.
Figure 11:
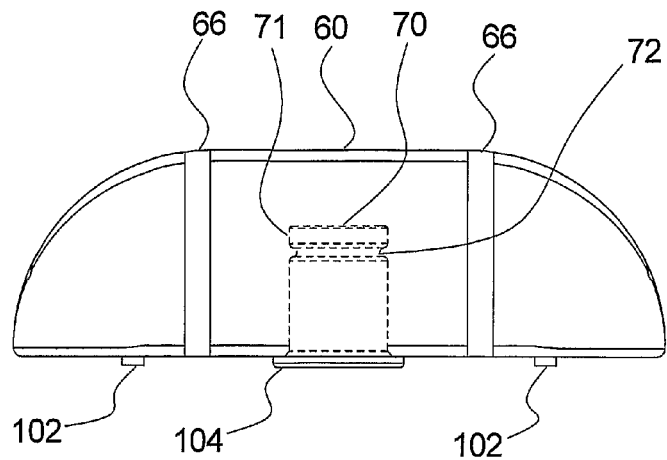
FIG. 11 is a side view of the line retaining part shown in FIG. 10.
Figure 12:
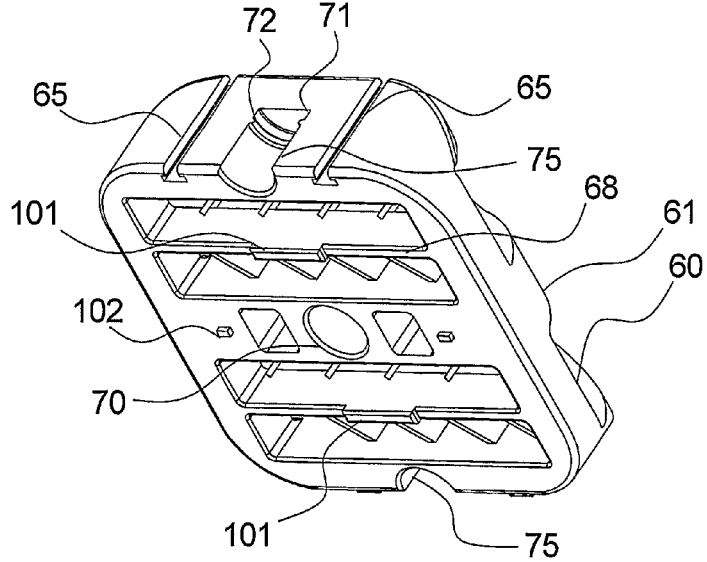
FIG. 12 is a perspective view from below of the line retaining part shown in FIG. 10.
Figure 13:
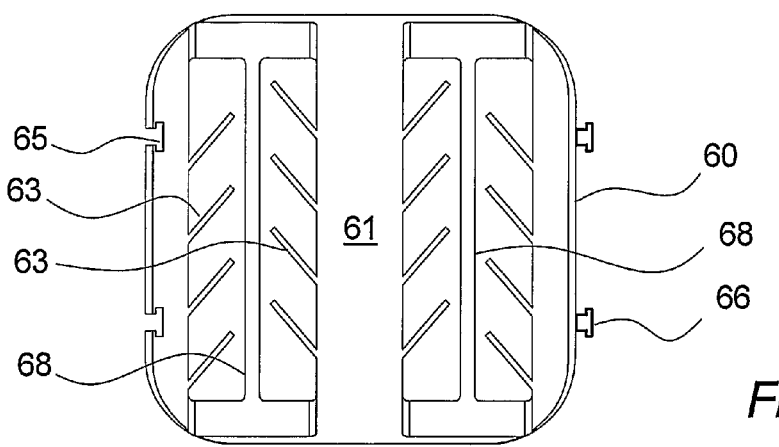
FIG. 13 is a view from above of the line retaining part shown in FIG. 10.

As shown in for example FIGS. 10 and 12, the line retaining part 60 may also comprise an indentation at the two side parts where the dovetails 66 and dovetail grooves 65 are located. These indentations each form a half part 75 of a snap lock cavity, corresponding to the snap lock cavity 70 located in the middle of the part 60. As shown, these half parts 75 comprises also a groove 71 and a rib 72, and it will be understood that when two line retaining parts 60 are connected to each other, these half parts 75 will together form a snap locking cavity corresponding to the one 70 located in the middle of the part 60, completely with an annular groove 71 and an annular rib 72. Thus, when two line retaining parts are connected together, e.g. with a total of four line retaining grooves 62, these may be located symmetrically on a base part 80 with the snap locking tap 94 engaging with the snap locking cavity formed by the two half parts 75.

Instead of using clamping means for locating the securing device 50 the base part 80 may be designed for being fixed to the patient or to an article in other suitable manners. For example, the base part 80 may be designed as a flexible clamp, e.g. an omega-shaped clamp that may be clamped onto a part of a structure, e.g. a rod or a tube that may form part of a bed or medical equipment etc., or the base part may be designed as an adhesive part, with Velcro means etc. Further, it will be understood that the securing device 50 may be adapted for being fixed to other means, e.g. to a band such as a head band, arm band etc. on a patient or a special base part adapted for being fixed to e.g. the ear of a patient. Other applications will be possible, which will be obvious to the skilled person.

Figures 22A, 22B:
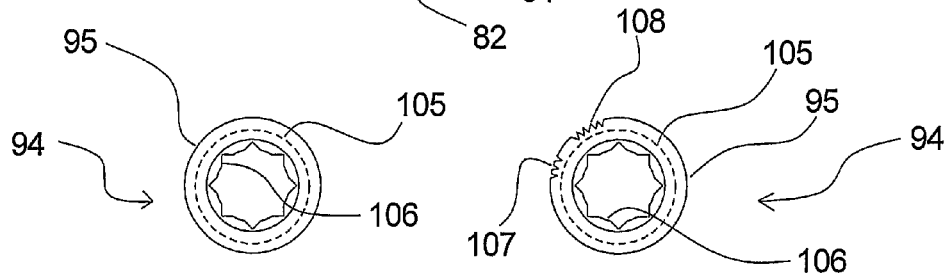
FIGS. 22a-b show different embodiments of the snap locking tap seen from above.

As shown in FIGS. 22a and 22b, the snap locking tap 94, which is here seen from above, may be designed with different modifications. As shown in FIG. 22a, the tap 94 is configured as a cylindrical body with an inner surface 106. In the outer surface, an annular groove 105 is provided as explained above, thereby providing an annular rib part 95. As shown in FIG. 22b, the outer surface of this annular rib part 95 may be adapted to allow an easy insertion of the snap locking tap 94 in the snap locking cavity 70. As indicated by the reference 107, the rib part 95 may be provided with cuttings or notches in such a manner that a coarse toothed edge 107 is provided or as indicated by the reference 108 in such a manner that a fine toothed edge 108 is provided. It will be understood that such a toothing will occupy the complete rib and not just the local regions indicated in FIG. 22b. Hereby it is achieved that the teeth will flex when the snap locking tap 94 is inserted in the snap locking cavity 70 and entered in the annular groove 71.

Figure 23:
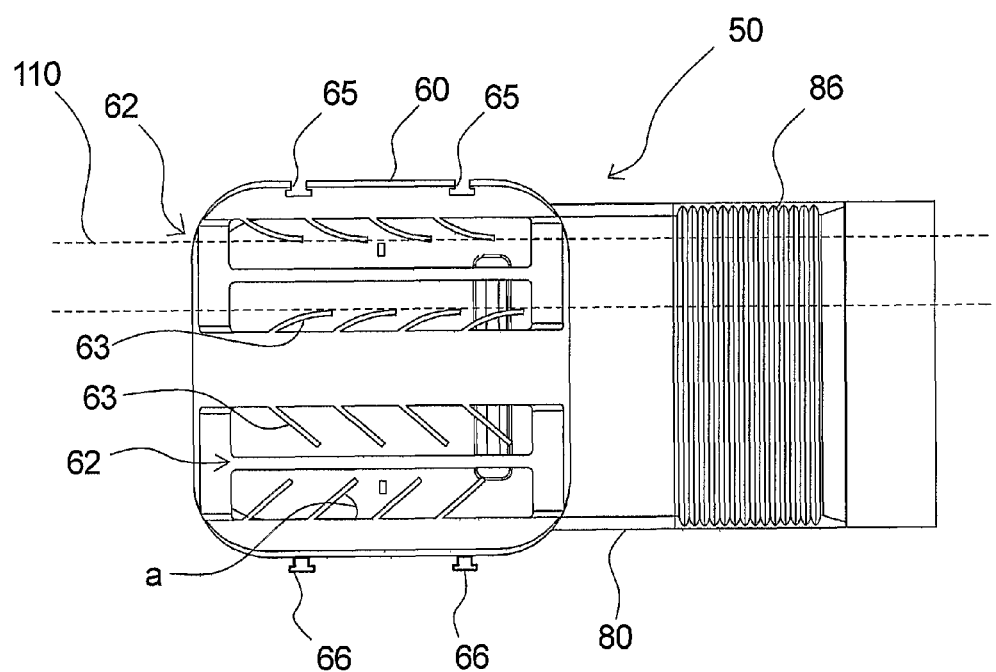
FIG. 23 is a view from above of the device shown in FIG. 6, but with a line indicated in one of the grooves.

In FIG. 23 a device according to an embodiment of the invention is shown in a view from above corresponding to FIG. 6. Here, a line 110 such as a medical line, a tube, a catheter, a wire etc. is shown with dotted lines in the upper groove 62 in the drawing. Thus, it is shown that the flexible blades 63 are elastically forced towards the sides of the groove 62. Further, it will be understood that the line 110 will be held in a firm grip by the blades 63, but further it will be understood that as explained above the tip of the blades 63 will provide a firmer grip in the line 110 if a pull is exerted in the line in a direction towards the left in the drawing. Further, it will be seen from FIG. 23 that the grooves 62 may accommodate a wide range of lines, e.g. as regard the width of the lines, e.g. from a width barely larger than the distance between the tips of the blades 63 shown in the lower groove in FIG. 23 to a width corresponding nearly to the width of the groove, although taking into account the thickness of the blades 63.

Above, the securing device 50 has been illustrated with grooves having flexible blades 63 located at both sides of the groove 62, but as also mentioned above, embodiments having flexible blades at only one side of the groove 62 are also possible in accordance with the invention. When such embodiments are concerned, the flexible blades may for example be fixed to the outer wall of the line retaining part 60 and angled towards the centre beam 61. This centre beam 61 may in such embodiments be designed with a flat top part that is wider than the underlying part and in such a manner that the edges of the flexible blades, e.g. the edges 69 shown in FIG. 3c, are located under the top part. Thus, after a line has been inserted in the groove 62, the flexible blades 63 will—at least for some tube sizes—flex back to a position where the outer edge of the blade is located under the top part of the centre beam. In this manner the line will be secured by the flexible blades pressing against the line. But also, the line will be further secured since the line will be prevented from leaving the groove since the blades will lock the line in the vertical direction, i.e. caused by the interaction between the top part of the centre beam and the outer edges of the flexible blades. It is obvious that a similar embodiment may be designed when the flexible blades are located at the centre beam with their edges pointing towards an outer wall of the line retaining part.

Further, it should be mentioned that the centre beam may serve for informational purposes, e.g. the name of the manufacturer, e.g. HED, or the purpose, application etc., of the device may be printed, embossed or moulded here.

Still further, it is noted that the securing device according to the invention may be combined with or integrated with other devices, for example in the medical field. In particular, electronic or similar devices, sensors etc. may be integrated with the device, for example in order to facilitate diagnosis, monitoring etc. Such means may relate to flow monitoring, temperature measurements, electromagnetic measuring devices etc.

It will be understood that the invention is not limited to the particular examples described above and shown in the drawings but may be modified in numerous manners, used in a wide variety of applications and manufactured in materials commonly used with the medical and neighboring fields as also indicated above. Thus, it will be understood that the device according to the invention may be designed in a multitude of varieties within the scope of the invention as specified in the claims.

The invention claimed is:
1. Device for securing a medical line, said device comprising
    a line retaining part and a base part,
    said line retaining part comprising at least one groove for accommodating the line, each of said at least one grooves including a major longitudinal axis that corresponds to a major longitudinal axis of the medical line, each of said at least one grooves further including openings that open to an ambient environment at opposing groove sides, said openings and said groove sides being situated relatively parallel to said major longitudinal axis of said at least one groove,
    wherein each opening is disposed to face the other opposing opening along an axis perpendicular to said major longitudinal axis of said at least one groove, and
    wherein said groove is configured to receive the line via at least one of said openings,
    said base part comprising fixing means,
    wherein said line retaining part and said base part are provided with complementary locking means for providing a connection between said line retaining part and said base part, and
    wherein said at least one groove is designed with flexible retaining means for retaining the line;
    wherein the flexible retaining means for retaining the line comprises a plurality of flexible parts protruding into the groove, and
    wherein at least one of said openings is configured to remain open while the line is releasably retained in said groove.
2. Device according to claim 1, wherein said protruding flexible parts are placed essentially lateral of the groove.
3. Device according to claim 2, wherein said protruding flexible parts are designed as blades that protrude into the groove.
4. Device according to claim 3, wherein said protruding flexible blades are located at an angle in relation to an axis of the groove.
5. Device according to claim 4, wherein said angle of the flexible blades in relation to the axis of the groove is in an interval of 10°-80°.
6. Device according to claim 1, wherein said flexible retaining means are placed only at one side of the groove.
7. Device according to claim 1, wherein said flexible retaining means, are placed at both sides of the groove.
8. Device according to claim 1, wherein said line retaining part comprises only one groove for accommodating a line.
9. Device according to claim 1, wherein said line retaining part comprises at least two grooves for accommodating a line each, said grooves preferably being placed essentially in parallel.
10. Device according to claim 1, wherein said line retaining part is made of a polymeric material.
11. Device according to claim 1, wherein said complementary locking means of said line retaining part and said base part comprises snap locking means.
12. Device according to claim 11, wherein said snap locking means comprises a tap placed on said base part and a cavity in the line retaining part or vice versa.
13. Device according to claim 12, wherein said tap comprises a protruding annular part and said cavity comprises a complementary annular groove or vice versa.
14. Device according to claim 11, wherein said complementary locking means of said line retaining part and said base part are designed as a swivel joint, allowing the line retaining part to be adjusted in relation to said base part.
15. Device according to claim 14, wherein said line retaining part and said base part are designed with limit stops for said swivel joint, allowing the line retaining part to be adjusted within a limited angular range in relation to said base part.
16. Device according to claim 14, wherein said line retaining part and said base part are designed with interacting means, a toothed ring, cogging or similar means, that allows a relative movement and facilitate a parking of the line retaining part at certain angles in relation to said base part.
17. Device according to claim 1, wherein said fixing means of said base part comprises two opposing jaw parts that are forced together by spring means.
18. Device according to claim 17, wherein said spring means comprises a flexible connecting part between the two jaw parts.
19. Device according to claim 17, wherein said spring means comprises a flexible spring part connected to one of the two jaw parts and acting on the other jaw part.
20. Device according to claim 17, wherein said fixing means of said base part comprises a hinge means comprising hinge parts on both jaw parts.
21. Device according to claim 20, wherein said hinge parts on the jaw parts are designed as a hook element formed on one of the jaws and a corresponding opening formed on the other jaw.
22. Device according to claim 17, wherein said base part is formed as a flexible elongated part, ends of which form the jaw parts and an intermediate part forming a flexible part.
23. Device according to claim 22, wherein said base part is made of a polymeric material.
24. Device according to claim 1, wherein said fixing means of said base part comprises spring-loaded or flexible means that may be clipped onto structural parts.
25. Device according to claim 1, wherein said fixing means of said base part comprises adhesive means that may be applied onto structural parts or other articles.
26. Device according to claim 1, wherein said fixing means of said base part comprises mechanical means for securing the base part to an item at, on or near a patient.
27. Device according to claim 1, wherein said line retaining part comprises connection means on a side part for mechanically connecting said retaining part to a further retaining part.
28. Device according to claim 27, wherein said connection means comprises first connection means on a first side part and second connection means on a second side part, said first and second connection means being complementary.
29. Device according to claim 28, wherein said first and second connection means are designed as dovetail joints.
30. Device according to claim 27, wherein said line retaining part comprises a side part that is designed in order to form a part of said complementary locking means when said line retaining part is connected with a similar or identical line retaining part.
31. Device according to claim 1, wherein said line retaining part comprises further means for withholding a line in said groove.
32. Device according to claim 31, wherein said further means for withholding a line in said groove comprises a lid part, said lid part being connected to the line retaining part by a hinge.

* * * * *